United States Patent [19]

Cabezas

[11] Patent Number: 5,250,442
[45] Date of Patent: Oct. 5, 1993

[54] METHOD OF TREATING RHEUMATOID ARTHRITIS USING TETRACYCLINE

[76] Inventor: Orestes Cabezas, 10201 Fontainebleau Blvd., Unit 205, Miami, Fla. 33172

[21] Appl. No.: 44,054

[22] Filed: Apr. 8, 1993

[51] Int. Cl.$^5$ .................. G01N 33/564; A61K 31/65
[52] U.S. Cl. .................. 436/509; 514/152; 514/825
[58] Field of Search .............. 436/509; 514/152, 825

[56] References Cited

PUBLICATIONS

Dialoge Medicine File Abst. 90189067 (1990).

Primary Examiner—Frederick E. Waddell
Assistant Examiner—Gregory Hook
Attorney, Agent, or Firm—Malloy & Malloy

[57] ABSTRACT

A method of treating rheumatoid arthritis which includes first, taking a blood test to determine a rate of erythrocyte sedimentation and a rheumatoid factor, and then fasting for a 12-hour period prior to orally administering a 500 milligram dosage of tetracycline achromycin, and observing any change in the symptoms of the rheumatoid arthritis including reduction of swelling and pain in the affected sites. This process is repeated over 24-hour cycles until the rheumatoid factor has decreased by at least 50% from the first determined level prior to treatment and erythrocyte sedimentation decreased, at which point the 24-hour cycles are continued, reducing the dosage of tetracycline achromycin to 250 milligrams until the symptoms of the rheumatoid arthritis condition disappear.

3 Claims, No Drawings

METHOD OF TREATING RHEUMATOID ARTHRITIS USING TETRACYCLINE

BACKGROUND OF THE INVENTION

The present invention relates to a method for treating rheumatoid arthritis to alleviate the symptoms thereof.

Presently, an estimated 7,000,000 Americans suffer from rheumatoid arthritis. The symptoms of rheumatoid arthritis including pain and swelling of the smaller joints in the hands and feet. The affected joints become swollen, painful and warm to the touch during the initial attack and ensuing flare-ups. Often, the joints in the hands and the feet will ache or become stiff after extended periods of motionless such as after sleeping.

Rheumatoid arthritis is believed to be an autoimmune disease in which the body's immune system literally attacks itself. It is believed that rheumatoid arthritis initially develops from a virus which upsets the immune system. In response, the body's disease fighting cells attack the joints causing inflammation.

The primary area of attack of the disease fighting cells is the synovium, a smooth membrane which lines the joints and becomes inflamed during an onset of a attack of rheumatoid arthritis. Over time, if the disorder is chronic, the tissue in the cartilage begins to proliferate, causing the surrounding ligaments, bones, and muscles to deteriorate. Eventually, after extensive damage, the joints may become permanently loosened.

It has been found that just prior to and during the onset of an attack of rheumatoid arthritis, the rate of erythrocyte sedimentation is higher than normal. Additionally, about 85% of patients diagnosed with rheumatoid arthritis exhibit an antibody during an attack of rheumatoid arthritis referred to as rheumatoid factor.

Presently, rheumatoid arthritis is treated with aspirin and in many case with systemic corticosteroid drugs including prednisone. Corticosteroid drugs have been found to be very effective for relieving the pain and inflammation associated with rheumatoid arthritis. However, these drugs do not provide any permanent or longlasting positive results, but are merely effective in alleviating the symptoms during an attack of the rheumatoid arthritis disorder. Use of corticosteroid drugs, including prednisone, over an extended period of time, can be very dangerous as they have many detrimental side effects, including atrophy of the adrenal glands and loss of bone mineral and muscle weakness. Because the corticosteroid drugs are so effective in alleviating the pain, many patients have permanently damaged their joints by excessively using the joints during an attack of rheumatoid arthritis.

DETAILED DESCRIPTION OF THE PREFERRED EMBODIMENT

The present invention is directed to a method of treating rheumatoid arthritis. I have discovered that a patient having the disorder of rheumatoid arthritis may enjoy a disappearance of the symptoms by orally administering a predetermine dosage of tetracycline achromycin once every 24 hours over a period of about one to two weeks. If the symptoms disappear within this time, then further treatment is discontinued. As the symptoms begin to improve, the dosage may be decreased. I have found that the use of tetracycline achromycin on patients diagnosed with rheumatoid arthritis, and exhibiting rheumatoid factor and elevated erythrocyte sedimentation, has significantly diminished the inflammation and pain in the affected area while rapidly decreasing the rheumatoid factor and erythrocyte sedimentation rate. In most cases, the patient has recuperated fully from the disorder, except for isolated cases of rheumatoid arthritis which have been associated with other illnesses.

I have treated numerous patients in accordance with this method with the result that the symptoms of rheumatoid arthritis are significantly alleviated and in some cases, completely disappear. Additionally, I have found that the rheumatoid factor disappears in many patients after one to two months of treatment, and erythrocyte sedimentation rate decreases substantially. Seven criteria must be present t diagnose rheumatoid arthritis.

In all cases, the patient is first given a blood test to determine the erythrocyte sedimentation rate and rheumatoid factor. Next, the patient abstains from eating and drinking (except for water) for a period of 12 hours prior to initially administering a dosage of 500 milligrams of tetracycline achromycin. Fasting for 12 hours prior to administering the tetracycline achromycin is desirous so as to promote the maximum absorption of the drug into the patient's system. The patient is then observed daily to record any changes in the symptoms including reduction of swelling and pain in the effect joints. The dosage of 500 milligrams of tetracycline achromycin every 24 hours until the symptoms begin to improve. At this point, the rheumatoid factor and erythrocyte sedimentation rate is check to determine a decrease from the initial determination. Once the rheumatoid factor and erythrocyte sedimentation rate have decreased by at least 50% (in some cases, 70% may be preferable), then the dosage of tetracycline achromycin is reduced to 250 milligrams. The treatment cycle of fasting of 12 hours and then administering of dosage of 250 milligrams tetracycline achromycin is repeated daily until such time as the symptoms and rheumatoid factor disappear and erythrocyte sedimentation rate returns to normal. The blood is tested periodically throughout the treatment to determine the rheumatoid factor and erythrocyte sedimentation rate in order to monitor the progress of the treatment.

In one patient, the pain and swelling significantly reduced after three days of treatment. The rheumatoid factor dropped slightly after eight days of treatment. The symptoms gradually improved and after ten days, had practically disappeared. Treatment continued for another 25 days, testing the blood periodically, until the rheumatoid factor decreased by approximately 70% from the level first measured and erythrocyte sedimentation rate had dropped substantially. Treatment was continued, administering 250 milligrams of tetracycline achromycin every 24 hours until the rheumatoid factor disappeared and erythrocyte sedimentation rate lowered to normal levels. At this point, treatment was discontinued and the patient experienced no flare-ups of the rheumatoid arthritis disorder thereafter.

In another case, the patient was orally administered 500 milligrams of tetracycline achromycin once a day, in the morning hours prior to eating. After two weeks, the patient experienced significant improvements including a reduction in swelling of the joints in the hands and significantly greater mobility of the wrists and fingers. A blood test indicated a decrease of the rheumatoid factor as well as the rate of erythrocyte sedimentation. After six weeks, the rheumatoid factor decreased by 70% and the erythrocyte sedimentation rate had dropped, at which time the dosage of tetracycline achromycin was reduced to 250 milligrams. By the eighth week, the swelling and the pain had disappeared. Treatment was continued for one more week with no recurrence.

In all cases in which this method of treatment was used on patients, all medications which the patients were previously using were suspended prior to treatment in accordance with the method of the present invention. In cases where the patient was taking corticosteroids, such as prednisone, the dosages were gradually diminished to attain suspension, thereby preventing acute reactions which may result from sudden interruption, especially in patients taking substantially high dosages of prednisone. It was also observed that patients whom recuperated at an accelerated rate and whom had tended to lose sleep or awaken easily at night, due to the suffering of the symptoms of rheumatoid arthritis, did have trouble sleeping even after treatment, but soon became acclimated and thereafter able to sleep through the night.

I have found that the method of treatment of the present invention is also useful in treating rheumatoid arthritis associated with psoriasis vulgar is. The method of the present invention can be used in conjunction with my method for treating psoriasis as disclosed and claimed in U.S. Pat. No. 5,176,912.

It should be noted that in practicing the method of the present invention, the collateral effects of the prolonged use of tetracycline achromycin should be carefully evaluated and studied through laboratory testing. This is especially true in cases where substantially high dosages of administered for extended periods of over two months.

It is further emphasized that patients to be treated should be tested for hypersensitivity to various food substances and other allergies or irritants which may effect the arthritis symptoms. A balanced nutritional regimen is always useful, keeping in mind those foods which the patient may be hypersensitive too. It should be also noted that patients who have suffered from the rheumatoid arthritis disorder for a long period may become anemic, and therefore a balanced diet is extremely important.

While this invention has been shown and described in what is considered to be a practical and preferred embodiment, it is recognized that departures may be made within the spirit and scope of this method of treatment which should therefore not be limited except as set forth in the claims which follow hereinafter and within the doctrine of equivalents.

Now that the invention has been described,
What is claimed is:

1. A method of treating rheumatoid arthritis comprising the steps of:
    a) first, determining a rate of erythrocyte sedimentation and presence of rheumatoid factor in the blood;
    b) second, fasting for a period of 12 hours;
    c) third, orally administering a 500 milligram dosage of tetracycline achromycin every 24 hours after fasting for 12 hours;
    d) fourth, observing any change of symptoms of the rheumatoid arthritis condition including any reduction of swelling and pain;
    e) fifth, periodically testing the blood to determine a change in the rate of erythrocyte sedimentation and rheumatoid factor;
    f) sixth, repeat steps 1-5 until the rheumatoid factor and erythrocyte sedimentation rate has decreased by a predetermined percentage from the initial determination;
    g) seventh, after the rheumatoid factor and erythrocyte sedimentation rate has decreased by the predetermined percentage, reducing the dosage in step 3 to 250 milligrams; and
    h) eighth, continuing to orally administer a 250 milligram dosage every 24 hours, repeating steps 2, 4, 5 and 6, until the symptoms of the rheumatoid arthritis condition disappear.

2. The method of claim 1 wherein the predetermined percentage of decrease in the rheumatoid factor is at least 50%.

3. The method of claim 1 wherein the predetermined percentage of decrease in the rheumatoid factor is at least 70%.

* * * * *